United States Patent [19]

Isowa et al.

[11] 4,017,512

[45] Apr. 12, 1977

[54] PROCESS FOR PRODUCING N-ALKYLHYDROXYLAMINES

[75] Inventors: Yoshikazu Isowa, Funabashi; Hideaki Kurita, Sagamihara, both of Japan

[73] Assignee: Sagami Chemical Research Center, Tokyo, Japan

[22] Filed: July 1, 1975

[21] Appl. No.: 592,310

[30] Foreign Application Priority Data

July 2, 1974 Japan .............................. 49-74983
July 2, 1974 Japan .............................. 49-74984

[52] U.S. Cl. .................. 260/326 N; 260/326 S; 260/453 RW; 260/482 R; 260/534 M; 260/570.5 R; 260/583 DD

[51] Int. Cl.² ................ C07C 83/00; C07C 83/02; C07C 83/08; C07D 209/34

[58] Field of Search .... 260/583 DD, 556 A, 326 N, 260/326 S, 519, 534 M, 534 S, 470, 481 R, 326 N, 570.5 R, 534 M, 482 R

[56] References Cited

UNITED STATES PATENTS

| 3,312,738 | 4/1967 | Tishler et al. ................. 260/556 A |
| 3,617,190 | 11/1971 | Tesoyo et al. ................. 260/556 A |

OTHER PUBLICATIONS

Weisblat et al., "J.A.C.S.", vol. 75, pp. 3630–3632 (1953).

*Primary Examiner*—Dolph H. Torrence
*Attorney, Agent, or Firm*—Sughrue, Rothwell, Mion, Zinn & Macpeak

[57] ABSTRACT

A novel process for producing an N-alkylhydroxylamine of the formula (I)

RNH-OH             (I)

wherein R represents an alkyl group which may be substituted with least one substituent, which comprises reacting an N-mesyl-O-(p-alkoxybenzyl)hydroxylamine or an N-mesyl-O-(2,4,6-trialkylbenzyl)hydroxylamine with an alkyl halide of the formula (III)

RX                 (III)

wherein R is as defined above and X represents a halogen atom, under a basic condition to produce the corresponding N-alkyl-N-mesyl-O-(p-alkoxybenzyl)hydroxylamine or N-alkyl-N-mesyl-O-(2,4,6-trialkylbenzyl)hydroxylamine, and treating the resulting compound with a solution of a phenol compound, and novel N-alkyl-N-mesyl-O-(p-alkoxybenzyl)hydroxyl amines and N-alkyl-N-mesyl-O-(2,4,6-trialkylbenzyl)hydroxylamines which are useful as intermediates in the above process.

6 Claims, No Drawings

PROCESS FOR PRODUCING N-ALKYLHYDROXYLAMINES

BACKGROUND OF THE INVENTION

1. Field of the Invention

This invention relates to a novel process for producing N-alkylhydroxylamines represented by the formula (I)

RNH-OH         (I)

wherein R represents an alkyl group having 1 to 4 carbon atoms which may be substituted with at least one substituent, and to novel intermediates therefor.

2. Brief Description of the Prior Art

Hitherto, a wide variety of alkylhydroxylamines were known to be useful as starting materials and intermediates for producing various compounds. For example, 1-amino-3-hydroxylaminopropane is useful as an intermediate for the preparation of schizokinen which is known to be useful as a growth factor of fungi, and 2-amino-3-hydroxylaminopropionic acid is useful as a precursor for the synthesis of alanosine which is known to be useful as antiviral and antitumor agents. Further, 5-N-hydroxylornithine is useful as constituting a basic skeleton of rhodotorulic acid or ferrichrome. In general, most of the alkylhydroxylamines are important starting materials for the preparation of various pharmaceuticals, for example, ferrioxamines.

Typical conventional procedures for the preparation of alkylhydroxylamines include (1) a process comprising reduction of the corresponding nitro compound with zinc powder in the presence of ammonium chloride [W. Keller-Schierlein et al, Helv. Chim. Acta., 48, 710 (1965)], (2) a process comprising hydrolysis or hydrazinolysis of a nitron obtainable by the condensation of anti-benzaldoxime and an alkyl halide [C. N. Eaton et al, J. Med. Chem., 16, 289 (1973)], and (3) a process comprising reaction between an alkyl halide and hydroxylamine [G. C. Lanani, E. Lazzari and A. Diena, Farmaco, Ed. Sci., 24, 169 (1969)]. However, none of these conventional processes is advantageous in producing N-alkylhydroxylamines on an industrial scale. That is, in the conventional process (1) above, there are various problems in producing the necessary starting materials used in this process, i.e., nitro compounds, since silver nitrate must be used in producing these nitro compounds whereby the type of N-alkylhydroxylamines which are capable of being produced is markedly limited. In the conventional process (2) above, the anti-benzaldoxime used as a starting material is unstable and further only a DL-form of alkylhydroxylamines can be produced in this process since a strong alkali is used in the condensation of the alkyl halide and antibenzaldoxime. In the conventional process (3) above, side-reactions tend to occur thereby reducing the yield of the desired product and, therefore, this conventional process cannot be considered as an advantageous process for producing N-alkylhydroxylamines.

Summary of the Invention

An object of this invention is therefore to provide a novel process for producing N-alkylhydroxylamines which is advantageous in producing a wide variety of N-alkylhydroxylamines on an industrial scale and which is capable of producing the desired N-alkylhydroxylamines in high yields.

Another object of this invention is to provide a process for producing N-alkylhydroxylamines which can be applied to the production of an N-alkylhydroxylamine in either the L-form, the D-form or the DL-form.

A further object of this invention is to provide novel N-alkyl-N-mesyl-O-(p-alkoxybenzyl)hydroxylamines and N-alkyl-N-mesyl-(2,4,6-trialkylbenzyl)hydroxylamines of the formula (II) as hereinafter described which can be used for producing the N-alkylhydroxylamines of the formula (I) upon treatment with a solution of hydrogen bromide in an aliphatic acid in the presence of a phenol compound, and a process for producing the N-alkyl-N-mesyl-O-(p-alkoxybenzyl)hydroxylamines and N-alkyl-N-mesyl-O-(2,4,6-trialkylbenzyl)hydroxylamines of the formula (II).

DETAILED DESCRIPTION OF THE INVENTION

As a result of extensive studies on the process for producing N-alkylhydroxylamines, it was found that N-alkylhydroxylamines represented by the formula (I) can be effectively produced via intermediates of N-alkyl-N-mesyl-O-(p-alkoxybenzyl)hydroxylamines or N-alkyl-N-mesyl-O-(2,4,6-trialkylbenzyl)hydroxylamines as hereinafter described in greater detail.

According to the present invention, there is provided a process for producing an N-alkylhydroxylamine of the formula (I)

RNH—OH         (I)

wherein R represents a straight or branched chain alkyl group having 1 to 4 carbon atoms which can be substituted with at least one substitutent, which comprises reacting an N-mesyl-O-(p-alkoxybenzyl)hydroxylamine or an N-mesyl-O-(2,4,6-trialkylbenzyl)-hydroxylamine of the formula (IV)

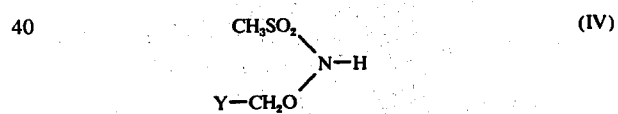
(IV)

wherein Y represents a p-alkoxyphenyl or 2,4,6-trialkylphenyl group having 1 to 4 carbon atoms in each of the alkyl moieties, with an alkyl halide of the formula (III)

R-X         (III)

wherein R is as defined above and X represents a halogen atom, under a basic condition to produce the corresponding N-alkyl-N-mesyl-O-(p-alkoxybenzyl)hydroxylamine or N-alkyl-N-mesyl-O-(2,4,6-trialkylbenzyl)hydroxylamine of the formula (II)

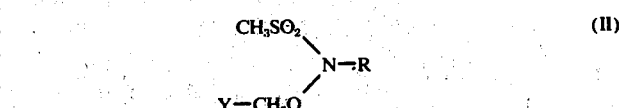
(II)

wherein Y and R are as defined above, and treating the resulting compound of the formula (II) above with a solution of hydrogen bromide in an aliphatic acid in the presence of a phenol compound.

The present invention also provides a novel N-alkyl-N-mesyl-O-(p-alkoxybenzyl)hydroxylamine or N-alkyl-N-mesyl-O-(2,4,6-trialkylbenzylhydroxylamine of the formula (II) above, and a process for producing the compound of the formula (II) which comprises reacting an N-mesyl-N-(p-alkoxybenzyl)hydroxylamine or N-mesyl-O-(2,4,6-trialkylbenzyl)hydroxylamine of the formula (IV) above with an alkyl halide of the formula (III) above, under a basic condition.

The present invention further provides a process for producing an N-alkylhydroxylamine of the formula (I) which comprises treating an N-alkyl-N-mesyl-O-(p-trialkylbenzyl)hydroxylamine or an N-alkyl-N-mesyl-O-(2,4,6-trialkylbenzyl)hydroxylamine of the formula (II) above with a solution of hydrogen bromide in an aliphatic acid in the presence of a phenol compound.

The processes of the present invention can be illustrated by the following reaction scheme wherein Y, R and X are as defined above.

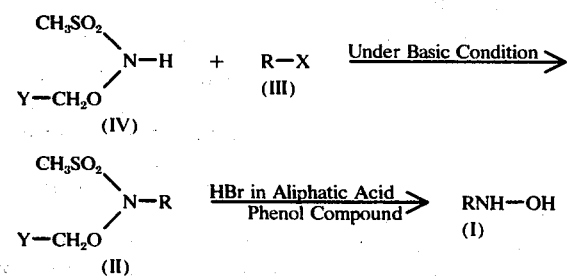

Although the exact mechanism of the removal of the protective groups upon treatment of the compound of the formula (II) with a HBr-aliphatic acid according to the process of this invention (conversion of the compound of Formula II to the compound of Formula I) is not clearly understood, this step is considered to be a reduction reaction. In the prior art reference, it was reported that a tosyl group can be used as a protective group for an amino group as illustrated below:

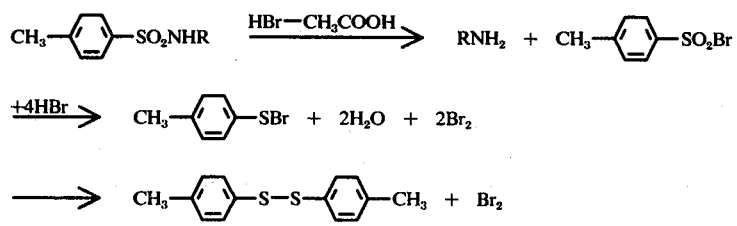

where the Br$_2$ formed during the reaction is removed with a phenol compound. On the other hand, it was known that the reaction between an N-mesylamine CH$_3$SO$_2$NHR and the HBr—CH$_3$COOH does not proceed to any appreciable degree and, therefore, a mesyl group has not been used as an N-protective group.

According to the present invention, it has been surprisingly found that the compound of the formula (II) can react with the HBr-aliphatic acid in the presence of a phenol compound to produce the desired compound of the formula (I), whereas no appreciable reaction occurs, except for undesirable side-reactions, when the compound having no Y—CH$_2$— group, i.e., the compound of the formula

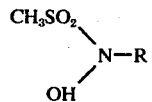

is used in place of the compound of the formula (II) in the process of this invention. The above fact clearly indicates that the O-protective group in the compound of the formula (II) i.e., a Y—CH$_2$— group, is not cleaved in advance to the removal of the mesyl group when the compound of the formula (II) is subjected to the treatment according to the process of this invention.

Further, it was found that an N-alkyl-N-mesyl-O-benzylhydroxylamine of the formula

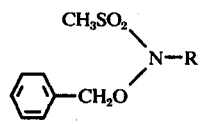

does not react with hydrogen bromide in an aliphatic acid. This fact indicates that, in the compound of the formula (II), removal of only a mesyl group would not take place in the process of this invention. Thus, it is understood that the O-protective group and the N-protective group in the compound of the formula (II) would be cleaved simultaneously upon treatment with a solution of hydrogen bromide in an aliphatic acid according to the process of this invention thereby resulting in the formation of the desired N-alkylhydroxylamines of the formula (I).

The starting materials of the formula (IV), i.e., N-mesyl-O-(p-alkoxybenzyl)hydroxylamines or N-mesyl-O-(2,4,6-trialkylbenzyl)hydroxylamines can be easily prepared by a well-known technique, for example, by reacting carboethoxyhydroxylamine with a p-alkoxybenzyl halide or a 2,4,6-trialkylbenzyl halide of the formula Y—CH$_2$Z wherein Y is as defined above and Z represents a halogen atom such as a chlorine atom, hydrolyzing the resulting product to obtain a p-alkoxybenzylhydroxylamine or 2,4,6-trialkylbenzyl-hydroxylamine of the formula Y—CH$_2$O—NH$_2$, and sulfonating the hydroxylamine thus obtained with a mesyl halide such as mesyl chloride using a well-known technique.

The starting materials of the formula (III), i.e., the alkyl halides are well known in the art and easily available as industrial materials.

Examples of the alkyl group for the substituent Y, i.e., p-alkoxyphenyl and 2,4,6-trialkylphenyl groups, are straight or branced chain alkyl groups having 1 to 4 carbon atoms, e.g., a methyl, ethyl, n-propyl, iso-propyl, n-butyl, sec-butyl and t-butyl groups, preferably a methyl group.

As described above, the characteristic feature of the process of this invention resides in that the mesyl group and the p-alkoxybenzyl or 2,4,6-trialkylbenzyl group present in the compound of the formula (II) as protective groups for the amino group and the hydroxyl group, respectively, can be cleaved smoothly and simultaneously upon treatment with a solution of hydrogen bromide in an aliphatic acid in the presence of a phenol compound at ambient temperature, i.e., without using elevated or cooled temperatures, thereby producing the desired N-alkylhydroxylamine of the formula (I) in high yield. Further, one of the features of the present invention is that the intermediate of the formula (II) can be optionally subjected to chemical reactions such as hydrazinolysis, acylation, optical resolution, etc., before the treatment with hydrogen bromide, in order to obtain a compound of the formula (II) having an alkyl group which is different from that of the alkyl (III) halide (III) and which is desired in the final product of the formula (I), as illustrated in Reference Examples 7, 8 and 9 hereinafter described.

As described previously, the alkyl group as the R group in the formulae (I), (II) and (III) above can be substituted with at least one substituent. Examples of the substituents are halogen atoms such as a chlorine atom, a bromine atom and the like, a phenyl group, a phthalimido group, a carboxyl group or an alkyl ester thereof having 1 to 4 carbon atoms in the alkyl moiety such as a methyl carboxylate group, an amino group and the like.

As is apparent to one skilled in the art, the reaction between the compound of the formula (IV) and an alkyl halide of the formula (III) can be effected with a wide variety of alkyl halides and the alkyl moiety (R) in the alkyl halide of the formula (III) can vary depending upon the desired alkyl group in the desired product of the formula (I). Thus, it is to be understood that the present invention is not limited to the use of a specific alkyl halide of the formula (III). Typical examples of alkyl halides of the formula (III) which can be used in the present invention are 1-phthalimido-3-bromopropane, benzyl halide, for example, benzyl chloride, dibromopropane, methyl 2,3-dibromopropionate and the like.

The reaction between the compound of the formula (IV) and the alkyl halide of the formula (III) can be carried out under a basic condition. Examples of bases which can be used in this reaction are alkali metal alkoxides such as sodium alkoxide, potassium alkoxides, e.g., a methoxide or an ethoxide, and the like, alkali metal hydroxides such as sodium hydroxide, potassium hydroxide and the like, alkali metal hydrides such as sodium hydride and the like.

In the reaction between the compound of the formula (IV) and the alkyl halide of the formula (III), the alkyl halide can be used in an amount of approximately an equimolar amount to a slightly excess amount with respect to the compound of the formula (IV), i.e., in the range of from about 1 to about 2 moles per moles of the compound of the formula (IV). The reaction is generally carried out in the presence of an inert solvent which does not adversely affect the reaction and the product, for example, alcohols such as methanol, ethanol, propanol and the like, tetrahydrofuran, dimethylformamide and the like at a temperature of from about 0° C to about 200° C, preferably from room temperature to refluxing temperature of the solvent used. The reaction time varies widely depending upon the reaction temperature used, but generally is from about 3 to about 12 hours. After completion of the reaction, the compound of the formula (II) thus obtained can be separated from the reaction mixture by conventional techniques, for example, distillation of the solvent used, extraction of the resulting residue with an organic solvent such as ethyl acetate and the like followed by concentration of the extract.

The subsequent treatment of the compound of the formula (II) obtained above with a solution of hydrogen bromide in an aliphatic acid can be carried out at an ambient temperature, i.e., at approximately room temperature (about 20°–30° C). An elevated temperature or a cooled temperature may also be used, but no advantage would be realized in using such temperature. The time required for the treatment generally is in the range of from about 15 to about 40 hours. As set forth previously, the protective groups for the amino group and the hydroxy group, i.e., a mesyl group and a p-alkoxybenzyl group or a 2,4,6-trialkylbenzyl group, can be cleaved simultaneously and smoothly to produce the desired N-alkylhydroxylamine of the formula (I).

The concentration of hydrogen bromide in the aliphatic acid can range from about 18 to about 36% by weight, but a concentration less than about 18% can be used although the reaction tends to proceed slowly.

The aliphatic acids which can be used in this treatment are those having 2 to 3 carbon atoms, for example, acetic acid and propionic acid, preferably, acetic acid.

Examples of phenol compounds which can be used in the treatment are phenol, naphthol, catechol and the like, preferably, phenol.

The solution of hydrogen bromide and the phenol compound are preferably used in a molar excess amount with respect to the compound of the formula (II), but the amount is not critical.

The product of the formula (I) thus obtained can be isolated from the reaction mixture using well-known techniques, for example, by filtration when the product is precipitated from the reaction mixture or adding anhydrous diethyl ether to the reaction mixture to precipitate the product followed by filtration. Alternatively, the solvent is first removed by evaporation and adding water and diethyl ether to remove the phenol compound and neutralizing carefully the product in the hydrobromide salt form contained in the aqueous layer with aqueous ammonia to obtain the desired product. It is to be noted, however, that the above-described procedures for the isolation and recovery of the product are given for illustrative purposes only and the present invention is not limited to such specific procedures.

The present invention is further illustrated by the following examples, but they are given for illustrative purposes only and are not to be construed as limiting the scope of this invention. Unless otherwise indicated, all parts, percents, ratios and the like are by weight.

REFERENCE EXAMPLE 1

Preparation of N-carboethoxy-O-(2,4,6-trimethylbenzyl)hydroxylamine 50 ml of a methanolic solution of 12.3 g (0.22 mole) of potassium hydroxide was added to 50 ml of an ice-cooled methanolic solution of 23.1 g (0.22 mole) of N-carboethoxyhydroxylamine to prepare a solution containing a potassium salt of N-carboethoxyhydroxylamine, and 50 ml of a methanolic solution of 33.7 g (0.2 mole) of 2,4,6-trimethylbenzyl chloride was added to the resulting solution at room temperature. The resulting mixture was heated under refluxing for 1 hour, and the solvent was distilled off. 150 ml of diethyl ether and 50 ml of water were then added to the residue and the organic layer was separated, dried over anhydrous sodium sulfate and concentrated under a reduced pressure. The residue thus obtained was distilled under a reduced pressure to obtain 25.5 g (53.8% yield) of substantially pure N-carboethoxy-O-(2,4,6-trimethylbenzyl)hydroxylamine having a boiling point of 148°–153° C/0.9 mmHg.

Elementary Analysis: Calcd. for $C_{13}H_{19}NO_3$(%): C, 65.40; H, 7.78. Found: C, 65.80; H, 8.07.

REFERENCE EXAMPLE 2

In the same manner as described in Reference Example 1, but using p-methoxybenzyl chloride in place of the 2,4,6-trimethylbenzyl chloride, N-carboethoxy-O-(p-methoxybenzyl)-hydroxylamine was obtained.

REFERENCE EXAMPLE 3

Preparation of O-(2,4,6-trimethylbenzyl)hydroxylamine 200 ml of an aqueous solution of 45 g (0.8 mole) of potassium hydroxide was added to 47.5 g (0.2 mole) of the N-carboethoxy-O-(2,4,6-trimethylbenzyl)hydroxylamine prepared as described in Reference Example 1, and the mixture was heated under refluxing for 5 hours. The reaction mixture was allowed to stand for 12 hours, the precipitated crystals were collected by filtration and washed with water to obtain 23.6 g (70.6% yield) of O-(2,4,6-trimethylbenzyl)hydroxylamine. Recrystallization from diethyl ether-petroleum ether (1:3 by volume) yielded a product having a melting point of 54 –55° C which was subjected to elementary analysis.

Elementary Analysis: Calcd. for $C_{10}H_{15}NO$ (%): C, 72.51; H, 8.95; N, 8.23. Found (%): C, 72.69; H, 9.15; N, 8.48.

REFERENCE EXAMPLE 4

In the same manner as described in Reference Example 3, but using N-carboethoxy-O-(p-methoxybenzyl)-hydroxylamine in place of the N-carboethoxy-O-(2,4,6-trimethylbenzyl)-hydroxylamine, O-(p-methoxybenzyl)hydroxylamine was obtained.

REFERENCE EXAMPLE 5

Preparation of N-mesyl-O-(p-methoxybenzyl)hydroxylamine (IV)

63.0 g (0.55 mole) of mesyl chloride was added dropwise to a solution of 76.5 g (0.5 mole) of O-(p-methoxybenzyl)-hydroxylamine in 400 ml of pyridine while ice-cooling and stirring. After completion of the addition, the resulting mixture was stirred at room temperature (about 20°–30° C) for 5 hours and then the solvent was removed by distillation. 600 ml of ethyl acetate was added to the resulting residue, and the mixture was washed successively with 1N hydrochloric acid and water. The mixture was then dried and the solvent was distilled off to obtain 75 g (64.8% yield) of N-mesyl-O-(p-methoxybenzyl)hydroxylamine (IV) having a melting point of 114°–116° C.

Elementary Analysis: Calcd. for $C_9H_{13}NO_4S$ (%): C, 46.65; H, 5.78; N, 6.06. Found (%): C, 46.74; H, 5.66; N, 6.06.

REFERENCE EXAMPLE 6

In the same manner as described in Reference Example 5, but using O-(2,4,6-trimethylbenzyl)hydroxylamine prepared as described in Reference Example 3 in place of the O-(p-methoxybenzyl)hydroxylamine, N-mesyl-O-(2,4,6-trimethylbenzyl)hydroxylamine (IV) having a melting point of 120° C (after recrystallization from ethyl acetate) and the following analytical values was obtained (82.2% yield).

Calcd. for $C_{11}H_{17}NO_3S$ (%): C, 54.29; H, 7.04; N, 5.76: Found: (%): C, 54.59; H, 7.17; N, 5.65.

EXAMPLE 1

Preparation of N-benzyl-N-mesyl-O-(p-methoxybenzyl)hydroxylamine (II)

9.25 g (40 mmoles) of N-mesyl-O-(p-methoxybenzyl)hydroxylamine prepared as described in Reference Example 5 was added to sodium methoxide (prepared from 150 ml of absolute methanol and 1.2 g of sodium metal), and 6 g of benzyl chloride was then added to the mixture. The resulting mixture was heated under refluxing for 3 hours. The solvent was distilled off, and 150 ml of ethyl acetate and 50 ml of water were added to the residue. The organic layer was separated, dried over anhydrous sodium sulfate and concentrated to obtain 8.4 g (65.6% yield) of N-benzyl-N-mesyl-O-(p-methoxybenzyl)hydroxylamine having a melting point of 85°–87° C.

Elementary Analysis: Calc. for $C_{16}H_{19}NO_4S$ (%): C, 59.89; H, 5.79; N, 4.38. Found (%): C, 59.79; H, 5.96; N, 4.36.

EXAMPLE 2

Preparations of 2-bromo-3-(N-mesyl-N-p-methoxybenzyloxy)aminopropionic acid and DL-2-amino-3-(N-methyl-N-p-methoxybenzyloxy)aminopropionic acid 80.9 g (0.35 mole) of N-mesyl-O-(p-methoxybenzyl)-hydroxylamine prepared as described in Reference Example 5 was added to sodium ethoxide (prepared from 500 ml of absolute ethanol and 8.4 g of sodium metal), and 92 g (0.35 mole) of ethyl 2,3-dibromopropionate was added dropwise to the mixture while ice-cooling and stirring. After completion of the addition, the mixture was stirred at room temperature for 10 hours. 70 ml of 5N sodium hydroxide was then added to the mixture while ice-cooling to hydrolyze the ester and the resulting mixture was adjusted to a pH of 4 with 2.5M sulfuric acid. The solvent was distilled off, and 500 ml of ethyl acetate was added to the residue to extract 2-bromo-3-(N-p-methoxybenzyloxy)aminopropionic acid.

The product obtained above gave 52 g (46.3% yield) of DL-2-amino-3-(N-mesyl-N-p-methoxybenzyloxy)aminopropionic acid upon allowing the product to stand in 1000 ml of concentrated aqueous ammonia. Recrystallization from water yielded a product having a melting point of 190°–192° C (with decomposition).

Calcd. for $C_{12}H_{18}N_2O_6S$ (%): C, 45.52; H, 5.51; N, 8.64. Found: (%): C, 45.27; H, 5.51; N, 8.80.

EXAMPLE 3

11.5 g (50 mmoles) of N-mesyl-O-(p-methoxybenzyl)-hydroxylamine prepared as described in Reference Example 5 was added to sodium methoxide (prepared from 150 ml of absolute methanol and 1.38 g of sodium metal), and 13.4 g (50 mmoles) of 1-phthalimido-3-bromopropane was then added to the mixture. The resulting mixture was heated under refluxing for 4 hours. The solvent was distilled off, and 150 ml of ethyl acetate and 50 ml of water were added to the residue. The organic layer was separated, dried over anhydrous sodium sulfate and concentrated. The oily substance which remained after the concentration was dissolved in hot n-propanol and the resulting solution was allowed to cool to obtain 14.1 g (67.5% yield) of 1-phthalimido-3-[N-mesyl-N-(p-methoxybenzyloxy)-]aminopropane having a melting point of 106°–107° C.

Elementary Analysis: Calcd. for $C_{20}H_{22}N_2O_6S$ (%): C, 57.44; H, 5.30; N, 6.64. Found (%): C, 57.40; H, 5.30; N, 6.70.

REFERENCE EXAMPLE 7

Preparation of 1-amino-3-[N-mesyl-N-(p-methoxybenzyloxy)]aminopropane 4.19 g (10 mmoles) of 1-phthalimido-3-[N-mesyl-N-(p-methoxybenzyloxy)]aminopropane prepared as described in Example 3 and 5.5 g of hydrazine monohydrate were heated at a temperature of 50 to 55° C for 5 hours, and the resulting mixture was adjusted to a pH of 5 with acetic acid. The precipitate formed was separated by filtration, and the filtrate was concentrated under a reduced pressure. 30 ml of water was then added to the concentrate, and the mixture was adjusted to a pH of 8 with 7% aqueous ammonia and extracted twice with a 100 ml portion of ethyl acetate. The extract thus obtained was dried over anhydrous sodium sulfate and concentrated to obtain 1-amino-3-[N-mesyl-N-(p-methoxybenzyloxy)]aminopropane as an oily substance in substantially a quantative yield. The monohydrochloride of the product thus obtained had a melting point of 162°–165° C after recrystallized from methanoldiethyl ether (1:5 by volume) and the following analytical values.

Elementary Analysis: Calcd. for $C_{12}H_{20}N_2O_4S \cdot HCl$ (%): C, 44.16; H, 6.46; N, 9.06. Found (%): C, 44.37; H, 6.52; N, 8.63.

EXAMPLE 4

Preparation of 1-bromo-3-(N-mesyl-N-p-methoxybenzyloxy)-aminopropane 23.2 g (0.1 mole) of N-mesyl-O-(p-methoxybenzyl)-hydroxylamine prepared as described in Reference Example 5 was added to sodium ethoxide (prepared from 250 ml of absolute ethanol and 2.4 g of sodium metal), and 40.4 g (0.2 mole) of 1,3-dibromopropane was added to the mixture. The resulting mixture was heated under refluxing for 8 hours. The solvent was distilled off, and 300 ml of ethyl acetate and 100 ml of water were added to the residue. The organic layer was separated, washed with water and dried over anhydrous sodium sulfate. The solvent was distilled off under a reduced pressure to obtain an oily residue which then dissolved in hot n-propanol. The solution was allowed to cool to obtain 23 g (65.4% yield) of crystalline 1-bromo-3-(N-mesyl-N-p-methoxybenzyloxy)aminopropane having a melting point of 64°–66° C. A sample of the product thus obtained was recrystallized from n-propanol and subjected to elementary analysis.

Elementary Analysis: Calcd. for $C_{12}H_{18}NO_4SBr$ (%): C, 41.57; H, 5.26; N, 3.85. Found (%): C, 40.91; H, 5.15; N, 3.98.

REFERENCE EXAMPLE 8

31.8 g (0.1 mole) of DL-2-amino-3-(N-mesyl-N-p-methoxybenzyloxy)aminopropionic acid prepared as described in Example 2 was suspended in 150 ml of acetic acid, and 15 ml of acetic anhydride was added to the suspension at room temperature. After allowing the mixture to stand for 4 hours, the mixture was concentrated under a reduced pressure to obtain an oily substance which was then dissolved in a small amount of hot ethyl acetate. The resulting solution was allowed to cool to obtain 26 g (71.3% yield) of DL-2-acetylamino-3-(N-mesyl-N-p-methoxybenzyloxy)aminopropionic acid having a melting point of 163°–164° C.

Elementary Analysis: Calcd. for $C_{14}H_{20}N_2O_7S$ (%): C, 47.09; H, 5.44; N, 7.79. Found (%): C, 46.66; H, 5.59, N, 7.77.

REFERENCE EXAMPLE 9

Preparation of L-2-amino-3-(N-mesyl-N-p-methoxybenzyloxy)aminopropionic acid 9.0 g (0.025 mole) of DL-2-acetylamino-3-(N-mesyl-N-p-methoxybenzyloxy)aminopropionic acid prepared as described in Reference Example 8 was suspended in 150 ml of water and the suspension was adjusted to a pH of 7.4 with aqueous ammonia to obtain a homogeneous solution. 1 g of an acylase obtained from Genus Aspergillus was added to the solution, and the mixture was incubated at a temperature of 38° C for 48 hours. The precipitated crystals were collected by filtration, and recrystallized from water using activated carbon to obtain 1.42 g of L-2-amino-3-(N-mesyl-N-p-methoxybenzyloxy)aminopropionic acid having a melting point of 185°–186° C and a specific rotation of $[\alpha]_D^{20}$ −27.6° (c, 1 in acetic acid).

0.5 g of the acylase used above was further added to the mother liquid obtained from the filtration as described above and the mixture was shaken for 48 hours to obtain an additional 1.1 g of the same product (L-form), with the total yield of the product being 2.52 g (63.3%).

Elementary Analysis: Calcd. for $C_{12}H_{18}N_2O_6S \cdot 1/2 H_2O$ (%): C, 44.23; H, 5.69; N, 8.49. Found (%): C, 44.03; H, 5.85; N, 8.56.

EXAMPLE 5

Preparation of N-benzylhydroxylamine (I)

1.28 g (4 mmoles) of N-benzyl-N-mesyl-O-(p-methoxybenzylhydroxylamine prepared as described in Example 1 was treated with 15 ml of a 38% hydrogen bromide solution in acetic acid at room temperature for 20 hours in the presence of 1.5 g of phenol, and the mixture was then concentrated under a reduced pressure. 30 ml of diethyl ether and 10 ml of water and were then added to the resulting residue, and the aqueous layer was separated, concentrated under a reduced pressure to a small volume, adjusted to a pH of 8 with sodium carbonate and allowed to stand for 5 hours in a refrigerator. The crystals precipitated were collected by filtration to obtain 0.15 g (33% yield) of N-benzylhydroxylamine having a melting point of 56°–57° C. (The melting point reported in the literature is 57° C).

EXAMPLE 6

Preparation of 1-amino-3-hydroxyaminopropane Dihydrobromide 2.77 g (10 mmoles) of 1-amino-3-[N-mesyl-N-(p-methoxybenzyloxy)]aminopropane prepared as described in Reference Example 7 was treated with 25 ml of a 25% hydrogen bromide solution in acetic acid at room temperature for 40 hours in the presence of 4 g of phenol, and 200 ml of dehydrated diethyl ether was added to the mixture and the crystals precipitated were collected by filtration. The crystals thus obtained were washed repeatedly with dried diethyl ether to obtain 1.06 g (42.1% yield) of 1-amino-3-hydroxy aminopropane dihydrobromide. A sample of the product thus obtained recrystallized from methanol-diethyl ether (1:25 by volume) had a melting point of 157°–158° C. (The melting point reported in the literature is 157°–159° C.)

EXAMPLE 7

Preparation of DL-2-amino-3-hydroxyaminopropionic acid 1.91 g (6 mmoles) of DL-2-amino-3-[N-mesyl-N-(p-methoxybenzyloxy)]aminopropionic acid was treated with 15 ml of a 36% hydrogen bromide solution in acetic acid at room temperature for 40 hours in the presence of 2.4 g of phenol. The mixture was then concetrated under a reduced pressure and 15 ml of water and 30 ml of diethyl ether were added to the resulting residue. The aqueous layer was separated, concentrated to a small volume and adjusted to a pH of 8 with 7% aqueous ammonia while ice-cooling. Ethanol was then added to the resulting solution until the solution became a white turbid solution followed by allowing the mixture to stand. The precipitated crystals were collected by filtration to obtain 0.24 g (40% yield) of DL-2-amino-3-hydroxyaminopropionic acid having a melting point of 162°–164° C (with decomposition). (The melting point reported in the literature is 163° ° C with decomposition.)

EXAMPLE 8

Preparation of L-2-amino-3-hydroxyaminopropionic acid 1.91 g (6 mmoles) of L-2-amino-3-[N-mesyl-N-(p-methoxybenzyloxy)aminopropionic acid was treated with 30 ml of a 25% hydrogen bromide solution in acetic acid at room temperature for 70 hours in the presence of 2.4 g of phenol. The crystals precipitated were collected by filtration, washed with glacial acetic acid and dissolved in 15 ml of water. The solution was then worked up in the same manner as described in Example 7 to obtain 0.59 g (82% yield) of L-2-amino-3-hydroxyaminopropionic acid having a melting point of 168°–170° C (with decomposition) and a specific rotation of $[\alpha]_D^{28} \times 23.5°$ (c, 1 in 1N hydrochloric acid). (The melting point and the specific rotation reported in literature are 161°–163° C and ×15.7°, respectively.)

While the invention has been described in detail with reference to specific embodiments thereof, it will be apparent to one skilled in the art that various changes and modifications can be made therein without departing from the spirit and scope of the invention.

What is claimed is:

1. A process for producing an N-alkylhydroxylamine of the formula (I)

wherein R represents a straight or branched chain alkyl group having 1 to 4 carbon atoms which may be substituted with one or more substituents selected from the group consisting of a halogen atom, a phenyl group, a phthalimido group, a carboxyl group or an alkoxycarbonyl group having 1 to 4 carbon atoms in the alkoxy moiety thereof and an amino group, which comprises reacting an N-mesyl-O-(p-alkoxybenzyl)hydroxylamine or an N-mesyl-O-(2,4,6-trialkylbenzyl)hydroxylamine of the formula (IV)

wherein Y represents a p-alkoxyphenyl group or a 2,4,6-trialkylphenyl group, each having 1 to 4 carbon atoms in each of the alkyl moieties, with an alkyl halide of the formula (III)

wherein R is as defined above and X represents a halogen atom, in the presence of a base selected from the group consisting of an alkali metal alkoxide, an alkali metal hydroxide, an alkali metal hydride and a mixture thereof and in an inert solvent to produce the corresponding N-alkyl-N-mesyl-O-(p-alkoxybenzyl)hydroxylamine or N-alkyl-N-mesyl-O-(2,4,6-trialkylbenzyl)-hydroxylamine of the formula (II)

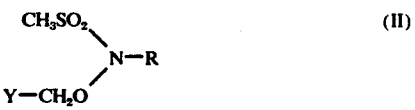

wherein Y and R are as defined above, and treating the resulting compound of the formula (II) above with a solution of hydrogen bromide in an aliphatic acid in the presence of a phenol compound.

2. The process according to claim 1, wherein said reaction is at a temperature of from about 0° C to about 200° C.

3. The process according to claim 1, wherein said alkyl halide of the formula (III) is used in an amount of from about 1 to about 2 moles per mole of said N-mesyl-O-(p-alkoxybenzyl)hydroxylamine or said N-mesyl-O-(2,4,6-trialkylbenzyl)hydroxylamine.

4. The process according to claim 1, wherein said solution of hydrogen bromide in an aliphatic acid has a hydrogen bromide concentration of from about 18 to about 36% by weight.

5. The process according to claim 1, wherein said aliphatic acid is acetic acid or propionic acid.

6. The process according to claim 1, wherein said treatment is conducted at ambient temperature for a period of from about 15 to about 40 hours.

* * * * *